(12) United States Patent
Pedersen

(10) Patent No.: US 11,643,633 B2
(45) Date of Patent: May 9, 2023

(54) DEVICE FOR MONITORING THE DEVELOPMENT OF A BIOLOGICAL MATERIAL

(71) Applicant: Esco Medical Technologies, UAB, Kaunas (LT)

(72) Inventor: Thomas William Pedersen, Skanderborg (DE)

(73) Assignee: ESCO MEDICAL TECHNOLOGIES, UAB, Kaunas (LT)

( * ) Notice: Subject to any disclaimer, the term of this patent is extended or adjusted under 35 U.S.C. 154(b) by 393 days.

(21) Appl. No.: 14/899,262

(22) PCT Filed: Jul. 5, 2013

(86) PCT No.: PCT/IB2013/055501
§ 371 (c)(1),
(2) Date: Dec. 17, 2015

(87) PCT Pub. No.: WO2015/001396
PCT Pub. Date: Jan. 8, 2015

(65) Prior Publication Data
US 2016/0145562 A1    May 26, 2016

(51) Int. Cl.
*C12M 1/34* (2006.01)
*C12M 1/02* (2006.01)
(Continued)

(52) U.S. Cl.
CPC ............ *C12M 41/46* (2013.01); *C12M 21/06* (2013.01); *C12M 23/10* (2013.01); *C12M 23/34* (2013.01);
(Continued)

(58) Field of Classification Search
CPC ...... C12M 23/10; C12M 23/34; C12M 23/38; C12M 29/00; C12M 29/04; C12M 29/20;
(Continued)

(56) References Cited

U.S. PATENT DOCUMENTS 4,720,462 A * 1/1988 Rosenson .............. C12M 21/08
                                                            435/286.6
6,166,761 A    12/2000 Arav
(Continued)

FOREIGN PATENT DOCUMENTS

WO        200140437 A2    6/2001
WO       2012047678 A2    4/2012

OTHER PUBLICATIONS

ESCO Medical: 11 Ferti 1 i tyjiVF Product, Catalogue 2013-2014 11, Jul. 1, 2013 (Jul. 1, 2013). XP002722518. Retrieved from the Internet: URL:http://www.escoglobal.comjimagesjupload/EnglishProductGuide.pdf, [retrieved on Mar. 31, 2014], p. 3.
(Continued)

*Primary Examiner* — Lydia Edwards
(74) *Attorney, Agent, or Firm* — Leason Ellis LLP

(57) ABSTRACT

The present invention relates to a device (100) for monitoring the development of a biological material, said device in the orientation intended for use comprising:

a housing (2) having an extension in a longitudinal direction (X) and an extension in a transversal direction (Y), said housing comprises:

two or more culture dish compartments (4), each adapted to accommodate a culture dish (6) comprising a biological material (8) to be monitored, each said compartment being separated from each of said other compartments, said two or more compartments being arranged along the longitudinal direction;

each said culture dish compartment (4) comprising a lid (10) adapted to be able to be shifted between an open configuration in which access to the interior (12) of said culture dish compartment is provided, and a closed configuration sealing off the interior of said culture dish compartment from its surroundings;

(Continued)

wherein each said culture dish compartment comprises an inlet (14) for supplying gas to and an outlet (16) for removing gas from said culture dish compartment;

wherein each said culture dish compartment comprising heating means (18) for heating the interior of said culture dish compartment;

wherein said housing comprises one or more cameras (20) for capturing images of a biological material in a culture dish.

36 Claims, 6 Drawing Sheets

(51) Int. Cl.
    *C12M 1/00*    (2006.01)
    *C12M 1/12*    (2006.01)
    *C12M 1/22*    (2006.01)
    *C12M 1/36*    (2006.01)
    *C12M 3/00*    (2006.01)

(52) U.S. Cl.
CPC ............ *C12M 23/38* (2013.01); *C12M 29/00* (2013.01); *C12M 29/04* (2013.01); *C12M 29/20* (2013.01); *C12M 29/26* (2013.01); *C12M 37/02* (2013.01); *C12M 41/14* (2013.01); *C12M 41/24* (2013.01); *C12M 41/34* (2013.01); *C12M 41/36* (2013.01); *C12M 41/48* (2013.01)

(58) Field of Classification Search
CPC ...... C12M 29/26; C12M 37/02; C12M 41/14; C12M 41/24; C12M 41/34; C12M 41/36; C12M 41/46; C12M 41/48
See application file for complete search history.

(56) References Cited

U.S. PATENT DOCUMENTS

| | | | |
|---|---|---|---|
| 2003/0039998 A1* | 2/2003 | Gelfand | C12Q 1/6886 435/6.13 |
| 2009/0311675 A1* | 12/2009 | Hosokawa | G01N 33/86 435/5 |
| 2011/0092762 A1 | 4/2011 | Wong | |
| 2012/0178150 A1* | 7/2012 | Tempelman | A01N 1/0226 435/286.1 |

OTHER PUBLICATIONS

ESCO Medical: "Miri. Multi-room incubator for IVF". Escoglobal.com, Feb. 27, 2013 (Feb. 27, 2013). XP002722519. Retrieved from the Internet: URL:http://www.escoglobal.comjproductsjdownload/1363707849.pdf, [retrieved on Mar. 31, 2014]. The whole document.

LabiVF Asia Pte. Ltd.: "G185 IVF Tri-Gas Incubator". Labivf.com Jan. 1, 2010 (Jan. 1, 2010). XP002722520. Retrieved from the Internet: URL:http://www.labivf.comjindex.cfm?GPID=23 [retrieved on Mar. 31, 2014]. The whole document.

Primo Vision: "Primo Vision Time-Lapse embryo monitoring system" Jan. 1, 2011 (Jan. 1, 2011). XP002722521. Retrieved from the Internet: URL:http://www.vitrolife.comjenjFertility/Products/Primo-Vision-Time-Lapse-System/ [retrieved on Mar. 31, 2014]. pp. 1-4.

* cited by examiner

DEVICE FOR MONITORING THE DEVELOPMENT OF A BIOLOGICAL MATERIAL

FIELD OF THE INVENTION

The preset invention relates in a first aspect to a device for monitoring the development of a biological material.

In a second aspect the present invention relates to a system comprising a device according to the first aspect according to the present invention combined with an image processing unit.

In a third aspect the present invention relates to such an image processing unit per se.

In a fourth aspect the present invention relates to a kit-of-parts comprising the device according to the first aspect of the present invention or comprising the system according to the second aspect of the present invention, in combination with a number of culture dishes configured to contain a biological material.

In a fifth aspect the present invention relates to the use of the device according to the first aspect of the present invention, or of the system according to the second aspect of the present invention, or of the kit-of-parts according to the fourth aspect of the present invention, for monitoring the development of a biological material.

Finally, in a sixth aspect the present invention relates to the use of an image processing unit according to the third aspect for processing images captured over time.

BACKGROUND OF THE INVENTION

Within the field of culturing biological matter it has been the practice for decades to employ incubators for accommodating one or more culture dishes in which the biological material is arranged under specified conditions. Such incubators typically comprise a compartment which may be temperature controlled by a control unit. Additionally, the interior of the compartment may be connected to one or more external sources of gases in order to ensure a desired atmosphere within said compartment.

Recently, also multi compartment incubators with gas regulation have been available on the market. An example of such a type of multi compartment incubator is manufactured by K-Systems under the model name G185. This incubator comprises ten separate compartments having five shared pair-wise temperature regulation in respect of pairs of compartments.

In the case of culturing embryos, such as human embryo in the process of in vitro fertilizations, it is common practice to culture a rather high number of conceived eggs originating from the same woman. This is so, because it is of paramount importance for the success of the in vitro fertilization treatment that the embryo or embryos being reinserted into the uterus of the woman are health and viable.

To this end, camera systems have been developed which are designed to capture a time lapse series of images of a culture dish arranged in such camera system. In these prior art time lapse systems one or more culture dishes are arranged in the system and an image of each well of each culture dish may be captured. By repeating this procedure at predetermined intervals, a time lapse series of images will eventually result.

Studying the development of an embryo by looking at its associated time lapse series of images will help a laboratory technician or an expert in the field of embryology to assess the health and viability of a specific embryo with the view to select such an embryo or number of embryos and insert it/them into the uterus of a woman.

The prior art camera systems available on the marked all rely on the principle of providing a fixed camera within the housing of the system and accommodate one or more culture dishes on an "arm" and subsequently move that arm in relation to the fixed camera in order to capture the desired images.

Until recently, such time lapse systems did not provide temperature regulation nor did they provide any gas regulation of the atmosphere of the interior of the compartment.

The device Embryoscope ESD2 marketed by Unisense Fertilitech provides an improvement in relation to the previously available time lapse systems. The Embryoscope ESD2 comprises a single compartment having temperature regulation as well as gas regulation and it further comprises camera means allowing acquisition of time lapse series of images of a total of six culture dishes each comprising twelve wells for accommodating twelve embryos each. The six culture dishes are arranged on an arm, which in turns moves in at least two directions in relation to a fixed camera in order to capture the time lapse series of images.

Although the Embryoscope ESD2 is an improvement in relation to the previously available time lapse camera systems, this system nevertheless represents a number of shortcomings.

This statement relies on the fact in that it has been found that even small deviations in the temperature and the atmosphere, compared to optimum conditions, may have an adverse effect in the quality of the development of an embryo.

In case it is desired to examine one or more biological materials of a single culture dish outside the interior of the compartment of the Embryoscope ESD2 system, one will need to open the lid allowing access to the interior of that compartment in order to remove the specific culture dish. Such an operation will imply a rather severe adverse impact on the quality of the development of the biological material accommodated in the remaining culture dishes.

Accordingly, in case one single culture dish is removed from Embryoscope ESD2, great and adverse impacts in respect of an altered temperature and atmospheric profile, deviating from the optimum profile, will result, which in turn may lead to an non-optimum development of the biological material remaining in the compartment of the Embryoscope ESD2.

Furthermore, for research purposes and in order to find optimized temperature and gas composition of the atmosphere in an vitro fertilization process of e.g. human eggs, it may be advantageous to conduct a huge number of experiments in which the growths condition is varied from one embryo to another, thus at least empirically and statistically allowing to assess the most optimum growth conditions of an embryo.

The Embryoscope ESD2 does not allow for such optimization experiments because every embryo in every culture well of the various culture dishes will essentially experience the same controlled growth conditions.

Accordingly, a need for an improved device for monitoring the development of a biological material persists.

BRIEF DESCRIPTION OF THE INVENTION

The above mentioned disadvantages are overcome by the present invention in its first, second, third, fourth, fifth and sixth aspect.

Accordingly, in a first aspect the present invention relates to a device for monitoring the development of a biological material, said device in the orientation intended for use comprising:

a housing having an extension in a longitudinal direction (X) and an extension in a transversal direction (Y), said housing comprises:

two or more culture dish compartments, each adapted to accommodate a culture dish comprising a biological material to be monitored, each said compartment being separated from each of said other compartments, said two or more compartments being arranged along the longitudinal direction;

each said culture dish compartment comprising a lid adapted to be able to be shifted between an open configuration in which access to the interior of said culture dish compartment is provided, and a closed configuration sealing off the interior of said culture dish compartment from its surroundings;

wherein each said culture dish compartment comprises an inlet for supplying gas to and an outlet for removing gas from said culture dish compartment;

wherein each said culture dish compartment comprising heating means for heating the interior of said culture dish compartment;

wherein said housing comprises one or more cameras for capturing images of a biological material in a culture dish.

In a second aspect, the present invention relates to a system comprising a device according to the first aspect of the present invention combined with an image processing unit;

wherein said image processing unit comprises a data processor; an input device, such as an alphanumeric keyboard, allowing a user to input operation instructions; and a display adapted to present information to a user;

wherein said image processing unit being configured to upload and store a number of images, said images being captured in a chronological order by a camera at different points in time, said images depicting different culture wells of a number of culture dishes;

wherein said image processing unit is adapted to sort the images into a number of groups each group representing images associated with the same culture well;

wherein said image processing unit in respect of each group of images is adapted to sort said images in a chronological time lapse series of images originating from the same culture well;

wherein said image processing unit is adapted to receive instructions from a user to present on said display, in respect of each culture well of a specific culture dish, an image belonging to a time lapse series of images associated with each of the culture wells of said specific culture dish, said specific culture dish being selected by a user;

wherein said image processing unit is adapted to present on said display, in respect of each culture well of said specific culture dish, an individual image belonging to a time lapse series of images associated with each of the culture wells of said specific culture dish selected by a user; wherein said individual image being presented on said display in a relatively small "window";

wherein said image processing unit is adapted to allow a user to select amongst those relatively small "windows" a specific selected individual image belonging to one time lapse series of images associated with a specific culture well of said selected culture dish;

wherein said image processing unit is adapted to present said specifically selected individual image belonging to one time lapse series of images associated with a specific culture well of said selected culture dish, wherein said specifically selected individual image being presented in a relatively large "window" on said display;

wherein said image processing unit is adapted to present said relatively large "window" on said display concurrently with presenting each of the relatively small "windows", each representing an image belonging to one time lapse series of images associated with the remaining culture wells of said selected culture dish;

wherein said image processing unit is adapted to receive instructions from a user relating to "playing" said time lapse series of images associated with said individual image being presented in said relatively large "window"; and wherein said image processing unit is adapted to, subsequently to "play" said time lapse series of images associated with said individual image being presented in said relatively large "window".

In a third aspect, the present invention relates to an image processing unit as defined in accordance with the second aspect.

In a fourth aspect, the present invention relates to a kit of parts comprising a device according to the first aspect of the present invention; or a system according to the second aspect of the present invention, combined with a number of culture dish configured to contain a biological material to be monitored.

In a fifth aspect, the present invention relates to the use of a device according to the first aspect of the present invention; or a system according to the second aspect of the present invention; or of a kit of parts according to the fourth aspect of the present invention, for monitoring the development of a biological material.

In a sixth aspect the present invention relates to the use of an image processing unit according to the third aspect for processing images captured over time.

In the device according to the first aspect of the present invention, each culture dish may be allocated its own individual compartment which may provide individual control of temperature and gas composition profile.

This feature thus implies overcoming the disadvantages mentioned above in respect of the prior art systems.

DETAILED DESCRIPTION OF THE INVENTION

Figure 1:
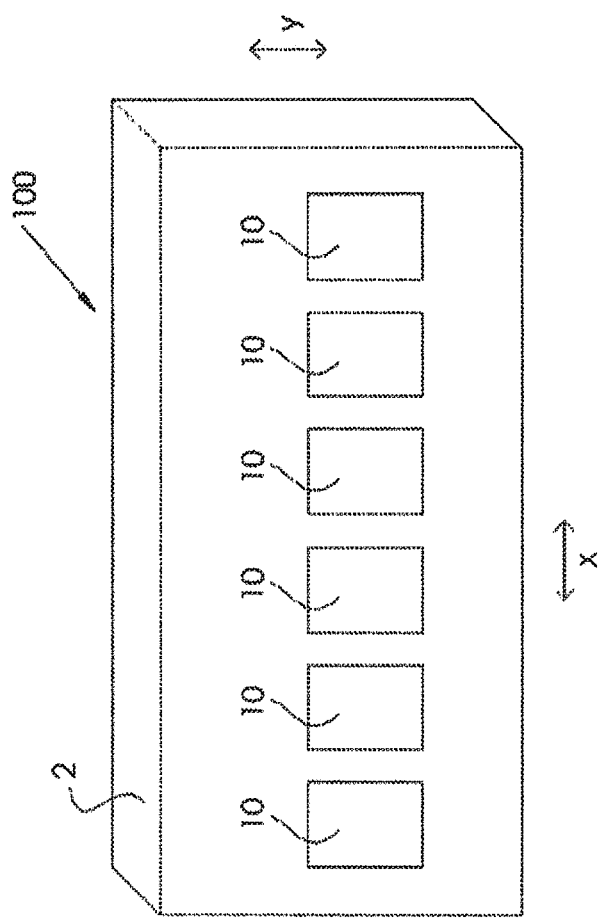
FIG. 1 shows in a perspective view an embodiment of the device according to the first aspect of the present invention.

The First Aspect of the Present Invention

In a first aspect the present invention relates to a device for monitoring the development of a biological material, said device in the orientation intended for use comprising:

a housing having an extension in a longitudinal direction (X) and an extension in a transversal direction (Y), said housing comprises:

two or more culture dish compartments, each adapted to accommodate a culture dish comprising a biological material to be monitored, each said compartment being separated from each of said other compartments, said two or more compartments being arranged along the longitudinal direction;

each said culture dish compartment comprising a lid adapted to be able to be shifted between an open configuration in which access to the interior of said culture dish compartment is provided, and a closed configuration sealing off the interior of said culture dish compartment from its surroundings;

wherein each said culture dish compartment comprises an inlet for supplying gas to and an outlet for removing gas from said culture dish compartment;

wherein each said culture dish compartment comprising heating means for heating the interior of said culture dish compartment;

wherein said housing comprises one or more cameras for capturing images of a biological material in a culture dish.

Accordingly, the present invention in its first aspect relates to a device for monitoring the development of a biological material. The device comprises a housing which houses two or more separate culture dish compartments. Each said culture dish compartment comprising a lid, a gas inlet and a gas outlet and heating means, wherein said housing comprises one or more cameras for capturing images of a biological material in a culture dish.

In the device according to the first aspect of the present invention it is preferred that the culture dishes are adapted to be stationary arranged within the culture dish compartments, whereas the camera is adapted to be moveable in relation the various culture dishes.

In the present description and in the appended claims, the term "in the orientation intended for use" shall be interpreted to mean in an orientation in which the device is arranged so that when a culture dish is accommodated in one of the shelves intended therefor, the culture dish will be oriented in an essentially horizontal direction having its open end pointing upward.

The device is especially suitable and intended for monitoring an embryo or one or more stem cells, such as an embryo or one or more stem cells of mammal origin, such as of human origin.

In one embodiment of the first aspect of the present invention, the number of culture dish compartments of the device is 3-20, such as 4-19, e.g. 5-18, such as 6-17, for example 7-16, e.g. 8-15, such as 9-14, for example 10-13 or 11-12.

Providing the device with a number of separate culture dish compartments corresponding to the above ranges will ensure great flexibility in that a number of culture dishes may be monitored at the same time.

In one embodiment of the first aspect of the present invention, said culture dish compartment in respect of one or more of said culture dish compartments, preferably all said culture dish compartments, comprises a shelf adapted to accommodate a culture dish, said shelf being provided with a heating means configured to heat said shelf.

Providing a culture dish compartment with a shelf for the culture dish allows for easy and save accommodation of such a culture dish in said compartment. In some embodiments, the shelf may consist of the bottom itself of the culture dish compartment. The heating means will ensure direct heating of the culture dish.

In one embodiment of the first aspect of the present invention, the lid in respect of one or more of said culture dish compartments, preferably all said culture dish compartments, is provided with heating means.

Providing the lid of the culture dish compartment with heating means will ensure that heat may be provided from the top as well as from the bottom of the compartment, implying more efficient and homogeneous temperature with the compartment.

In one embodiment of the first aspect of the present invention, a temperature sensor is provided in respect of one or more of said culture dish compartments, preferably all said culture dish compartments.

Providing a temperature sensor in a culture dish compartment will ensure a precise temperature control independent of each other culture dish compartments.

In one embodiment of the first aspect of the present invention, a pH sensor is provided in respect of one or more of said culture dish compartments, preferably all said culture dish compartments.

Providing a pH sensor in a culture dish compartment will enable a precise pH control of the culture medium in a well of a culture dish accommodated in said compartment.

In one embodiment of the first aspect of the present invention, said device comprises one or more connectors for supplying one or more types of different gases from an external source, such as from a gas cylinder.

Providing the device with one or more connectors for supplying one or more types of different gases from an external source will enable the interior of one or more of said compartment to have a desired atmosphere which will be suitable for the viability of the biological material to be cultured in one or more wells of a culture dish accommodated within the culture dish compartments of the device.

In one embodiment of the first aspect of the present invention, one or more of said one or more connectors are coupled to a valve located downstream of said connector for regulating the flow of gas into the apparatus.

Providing the device with a valve located downstream of a connector for supplying gas allows for controlling the composition of the gas atmosphere in the interior of a culture dish compartment with respect to the type of gas being supplied to that connector.

In one embodiment of the first aspect of the present invention, said device comprises a gas mixing box for said one or more gases, said gas mixing box optionally being located downstream in respect of said valve.

A gas mixing box will serve the purpose of providing thorough mixing of two or more gases being supplied to the culture dish compartments of the device.

In one embodiment of the first aspect of the present invention, said gas mixing box comprises a $CO_2$ sensor, such as a NDIR $CO_2$ sensor; and a $O_2$ sensor, such as a medical grade chemical $O_2$ sensor, and furthermore comprises one or more conduits for conducting a gas from said gas mixing box to one or more of said separate culture dish compartments.

Providing the gas mixing box with a $CO_2$ sensor and an $O_2$ sensor allows for controlling the gas atmosphere to be supplied to the interior of one or more culture dish compartments.

In one embodiment of the first aspect of the present invention, two or more culture dish compartments share the same gas mixing box; or alternatively each culture dish compartment is assigned its own individual gas mixing box.

Letting two or more culture dish compartments share the same gas mixing box will provide manufacturing savings to the device according to the invention. However, letting each culture dish compartment be assigned its own individual gas mixing box will allow a more precise control of individual culture dish compartments of the device.

In one embodiment of the first aspect of the present invention said apparatus comprises means for subjecting said one or more gas or mixture of gases to UV radiation, such as UV-C radiation, said means optionally comprises a filter filtering off any radiation which could lead to the production of ozone, such as UV radiation having a wavelength of 175-195 nm, such as UV radiation having a wavelength of 180-190 nm.

Exposing the gas for UV radiation will have a disinfecting effect on the gas.

In one embodiment of the first aspect of the present invention, the device furthermore comprising means for filtering the gas or mixture of gases, such as HEPA filter and/or a carbon filter.

This embodiment confers an additional sanitizing effect to the quality of the gas.

In one embodiment of the first aspect of the present invention said device in respect of one or more of said culture dish compartments comprises one or more conduits for leading gas from said culture dish compartment to a gas mixing box.

In one embodiment of the first aspect of the present invention, said device comprises one camera, said camera being attached to camera moving means for moving said camera along the area of the location of the culture dish compartments; said camera moving means being adapted to move said camera in at least a direction parallel to the longitudinal direction (X).

In one embodiment of the first aspect of the present invention, said camera moving means is adapted to move said camera below the area of the location of the culture dish compartments in a direction parallel to the longitudinal direction (X), and wherein in respect of one or more of said culture dish compartments at least part of the bottom of said culture dish compartments being transparent, thus allowing the camera to capture pictures of part of the culture dish from the position of said camera below said culture dish compartments.

It will be preferred to provide one and only one camera to the device. This camera will preferably be adapted to be allowed to move along a line defined by the positions of the wells of the culture dishes when these are accommodated in the interior of the culture dish compartments of the device. This line is preferably parallel to the longitudinal X direction of the device.

In one embodiment of the first aspect of the present invention, said one or more culture dish compartments comprising a camera, said camera being attached to camera moving means for moving said camera along the area of the location of the culture dish compartments within said compartments; said camera moving means being adapted to move said camera in at least one direction.

In one embodiment of the first aspect of the present invention, said device comprising a control unit for measuring and/or controlling one or more parameters of the operation of said device.

In one embodiment of the first aspect of the present invention, said one or more parameters are selected from the group comprising: temperature in the interior of one or more of said culture dish compartments; $O_2$ concentration in the in the interior of one or more of said culture dish compartments, $CO_2$ concentration in the in the interior of one or more of said culture dish compartments, pH in a culture medium present in a culture dish, magnitude of gas flow, magnitude of gas pressure, number of lid openings and duration of time thereof in respect of each specific lid, parameters of said camera, such as the frequency of image capturing by said camera, time of image acquisition.

In one embodiment of the first aspect of the present invention, said control unit is coupled to an input device, such as an alphanumerical keyboard, for allowing a user to define parameters of operation; and/or wherein said control unit is coupled to a display for providing information relating to the operation of the device to a user.

Providing the device with a control unit optionally also comprising an input device and/or a display will imply that very accurate control of the various parameters of operation of the device is possible.

The Second Aspect of the Present Invention

In a second aspect the present invention relates to a system comprising a device according to the first aspect of the present invention in combination with an image processing unit.

In the second aspect of the present invention, said image processing unit comprises a data processor; an input device, such as an alphanumeric keyboard, allowing a user to input operation instructions; and a display adapted to present information to a user;

wherein said image processing unit being configured to upload and store a number of images, said images being captured in a chronological order by a camera at different points in time, said images depicting different culture wells of a number of culture dishes;

wherein said image processing unit is adapted to sort the images into a number of groups each group representing images associated with the same culture well;

wherein said image processing unit in respect of each group of images is adapted to sort said images in a chronological time lapse series of images originating from the same culture well;

wherein said image processing unit is adapted to receive instructions from a user to present on said display, in respect of each culture well of a specific culture dish, an image belonging to a time lapse series of images associated with each of the culture wells of said specific culture dish, said specific culture dish being selected by a user;

wherein said image processing unit is adapted to present on said display, in respect of each culture well of said specific culture dish, an individual image belonging to a time lapse series of images associated with each of the culture wells of said specific culture dish selected by a user; wherein said individual image being presented on said display in a relatively small "window";

wherein said image processing unit is adapted to allow a user to select amongst those relatively small "windows" a specific selected individual image belonging to one time lapse series of images associated with a specific culture well of said selected culture dish;

wherein said image processing unit is adapted to present said specifically selected individual image belonging to one time lapse series of images associated with a specific culture well of said selected culture dish, wherein said specifically selected individual image being presented in a relatively large "window" on said display;

wherein said image processing unit is adapted to present said relatively large "window" on said display concurrently with presenting each of the relatively small "windows", each representing an image belonging to one time lapse series of images associated with the remaining culture wells of said selected culture dish;

wherein said image processing unit is adapted to receive instructions from a user relating to "playing" said time lapse series of images associated with said individual image being presented in said relatively large "window"; and wherein said image processing unit is adapted to, subsequently to "play" said time lapse series of images associated with said individual image being presented in said relatively large "window".

Accordingly, the image processing unit of the system according to the second aspect of the present invention allows handling of a large amount of images captured in respect of a number of culture wells of a number of culture dishes by a camera of the device according to the first aspect of the present invention.

The image processing unit is adapted to sort the amount of images captured into a number of time lapse series of images, wherein each sorted time lapse series of images relates to images captured in respect of a single culture well of a single culture dish accommodated within said device of the first aspect of the present invention.

Subsequently, the image processing unit of the system according to the second aspect of the present invention allows a user to select between the various series of time lapse images in order to further scrutinize the development of a biological material which has been cultured in the various wells of the various culture dishes which have been accommodated within said device according to a the first aspect of the present invention.

It should be noted that in the present description and in the appended claims, the term "series of time lapse images" may relate to a concrete electronic file comprising a number of individual concrete images, wherein said electronic file may be stored in a data storage. However, the in the present description and in the appended claims, the term "series of time lapse images" may also refer to a compilation of data storage addresses, wherein each storage address refers to a single image or a number of single images forming part of a time lapse series of images relating to images captured in respect of a single culture well of a single culture dish accommodated within said device of the first aspect of the present invention.

It should also be noted that in the present description and in the appended claims, the term "image" may be interpreted to mean a single image as captured by the image capturing means, such as by a camera; or alternatively, the term "image" may be interpreted to mean a Z-stack of images capture by merging a number of individual images representing the same subject and captured at essentially at the same point in time, but captured at different focus points in order to enhance the overall depth of field.

In one embodiment of the second aspect of the present invention, said image processing unit is adapted to receive instructions by a user to "play" said time lapse series of images associated with said individual image being presented in said relatively large "window" at a display rate selected by a user, said display rate being 0.1-30 frames per second (fps), such as 0.5-29 fps, e.g. 1-28 fps, such as 2-27 fps, e.g. 3-26 fps, for example 4-25 fps, such as 5-24 fps, e.g. 6-23 fps, such as 7-22 fps, for example 8-21 fps, such as 9-20 fps, for example 10-19 fps, such as 11-18 fps, e.g. 12-17 fps, for example 13-16 fps or 14-15 fps, either in a chronological forward or a chronological backward direction.

Such frequencies of displaying images have proven beneficial in relation to allow a user to get a good impression of the quality of the development of the biological material, when viewed as a time lapse series of images.

In one embodiment of the second aspect of the present invention, said image processing unit is adapted to receive instructions by a user relating to present in said relatively large "window" an image belonging to another time lapse series of images than the one actually being represented in said relative large "window", and wherein said image processing unit is adapted to, subsequently, to display an individual image belonging to said other time lapse series of images in said relatively large "window".

This feature allows user to have a good overview at the same time of all time lapse series of images captured in relating to all the culture wells of a single culture dish.

In one embodiment of the second aspect of the present invention, said image processing unit is adapted to received instructions by a user relating to one or more annotations of said specific image being displayed in said relatively "large window", wherein said image processing unit is adapted to, subsequently, to link and store such one or more annotations to said specific image.

In one embodiment of the second aspect of the present invention, said image processing unit is adapted to present on said display, any annotations associated with said specific image being presented in said relatively large "window".

In one embodiment of the second aspect of the present invention, said image processing unit is adapted to allow a user to edit, store and delete one or more annotations of said specific image being displayed in said relatively "large window", wherein said image processing unit is adapted to, subsequently, to link and store/delete such edition/deletion of one or more annotations to said specific image.

These features accordingly allow a user to link one or more comments to each image, and this in turn allows the user quickly to revert to previously images of interest.

In one embodiment of the second aspect of the present invention, said image processing unit, in respect of any one of said relatively small "windows", is adapted to present a marking of said relatively small "window" in the event that any annotations have been linked to one or more images in the time lapse series of images associated with the image presented in said relatively small "window", thus allowing a user to be informed that the time lapse series of images associated with said relatively small "window" has already been annotated.

In one embodiment of the second aspect of the present invention, said image processing unit is adapted to display one or more, such as two separate "windows" for presenting annotations associated with the specific image being presented in the relatively large "window".

These features relating to the annotations will allow a user easily to recognize those series of time lapse images in respect of which a user has already linked annotations to one or more images of that specific series of time lapse images.

In one embodiment of the second aspect of the present invention, said image processing unit is adapted to display the relatively small "windows" and the relatively large "window" in such a way that the relatively small "windows" surrounds the relatively large "window".

Such a layout will provide a very well-structured overview of the various time lapse series captured in respect of the various culture well of one culture dish.

In one embodiment of the second aspect of the present invention, said image processing unit is adapted to allow a user to scroll the list of annotations and to select one annotation, wherein said image processing unit is adapted to, subsequently, to display in the relatively large "window", the specific image linked to said selected annotation.

This feature will allow a user quickly to find specific images relating to events of special interest in respect of a specific time lapse series.

In one embodiment of the second aspect of the present invention, said image processing unit is adapted to have stored in a memory an "ideal time lapse series" corresponding to an ideal development over time, and wherein said image processing unit is adapted to present on said display, upon being instructed thereto, such an "ideal time lapse series", optionally as a superimposition of a time lapse series of images corresponding to said specifically selected culture well one the one hand and said "ideal time lapse series" on the other hand.

In one embodiment of the second aspect of the present invention, said "ideal time lapse series" is an authentic time lapse series or is an animated time lapse series, or a combination thereof.

These features accordingly allow a user to compare the development of a specific biological culture of a specific culture well of a specific culture dish, as represented by the specific time lapse series of images belonging to that specific biological material, with an "ideal time lapse series" representing what is believed to be an ideal development of the biological material. Hence, this feature allows a user to assess the quality of the development of a specific time lapse series.

It will be evident that the image processing unit disclosed above as part of the system according to the first aspect of the present invention, will just as well be suitable for use in combination with any such device for monitoring the development of a biological material, such as an incubator comprising image capturing means. For this reason, the present invention also relates to a system comprising the image processing unit as defined in respect of the second aspect of the present invention in combination with any kind of device for monitoring the development of a biological material, such as an incubator comprising image capturing means.

The Third Aspect of the Present Invention

In a third aspect the present invention relates to an image processing unit as defined in respect of the second aspect of the present invention.

The details of the invention according to the third aspect the present invention thus are as defined in respect of the image processing unit being part of the invention according to the second aspect of the present invention.

The Fourth Aspect of the Present Invention

In a fourth aspect the present invention relates to a kit of parts comprising a device according to any of the first aspect of the present invention; or a system according to any of second aspect of the present invention, combined with a number of culture dish configured to contain a biological material to be monitored.

In one embodiment of the fourth aspect of the present invention, said culture dishes having culture well depressions arranged on an essentially straight line.

In one embodiment of the fourth aspect of the present invention, said culture dishes comprises 4-26, such as 6-24, e.g. 8-22, for example 10-20, such as 12-18 or 14-16 culture well depressions, preferably all being arranged on an essentially straight line.

Using culture dishes in which the culture well depressions are arranged on an essentially straight line allow the culture dishes to be used in a device for monitoring the development of a biological material having image capturing means which is adapted to move in a single direction along the line of the culture well depressions of the various culture dishes.

The Fifth Aspect of the Present Invention

In a fifth aspect the present invention relates to the use of a device according to the first aspect of the present invention; or of a system according to the second aspect of the present invention; or of a kit of parts according to the fourth aspect of the present invention, for monitoring the development of a biological material.

In one embodiment of the fifth aspect of the present invention said biological material is an embryo or one or more stem cells, such as an embryo or one or more stem cells of a mammal, preferably of a human being.

The use has proven to be especially suitable for monitoring an embryo or one or more stem cells, such as an embryo or one or more stem cells of a mammal, preferably of a human being.

The Sixth Aspect of the Present Invention

In a sixth aspect the present invention relates to the use of an image processing unit according to the third aspect for processing images captured over time.

Referring now in details to the drawings for the purpose of illustrating preferred embodiments of the present invention, a device for monitoring the development of a biological material according to the first aspect of the present invention is shown in a perspective view in FIG. 1.

FIG. 1 shows in a perspective view an embodiment of a device 100 according to the first aspect of the present invention. FIG. 1 shows the housing 2 of the device 100. In the embodiment shown in FIG. 1 the device comprises 6 separate culture dish compartments 4, each having its own lid 10. The houses extends in a longitudinally direction X and in a transverse direction Y. The six separate culture dish compartments are aligned along the X direction.

Figure 2:
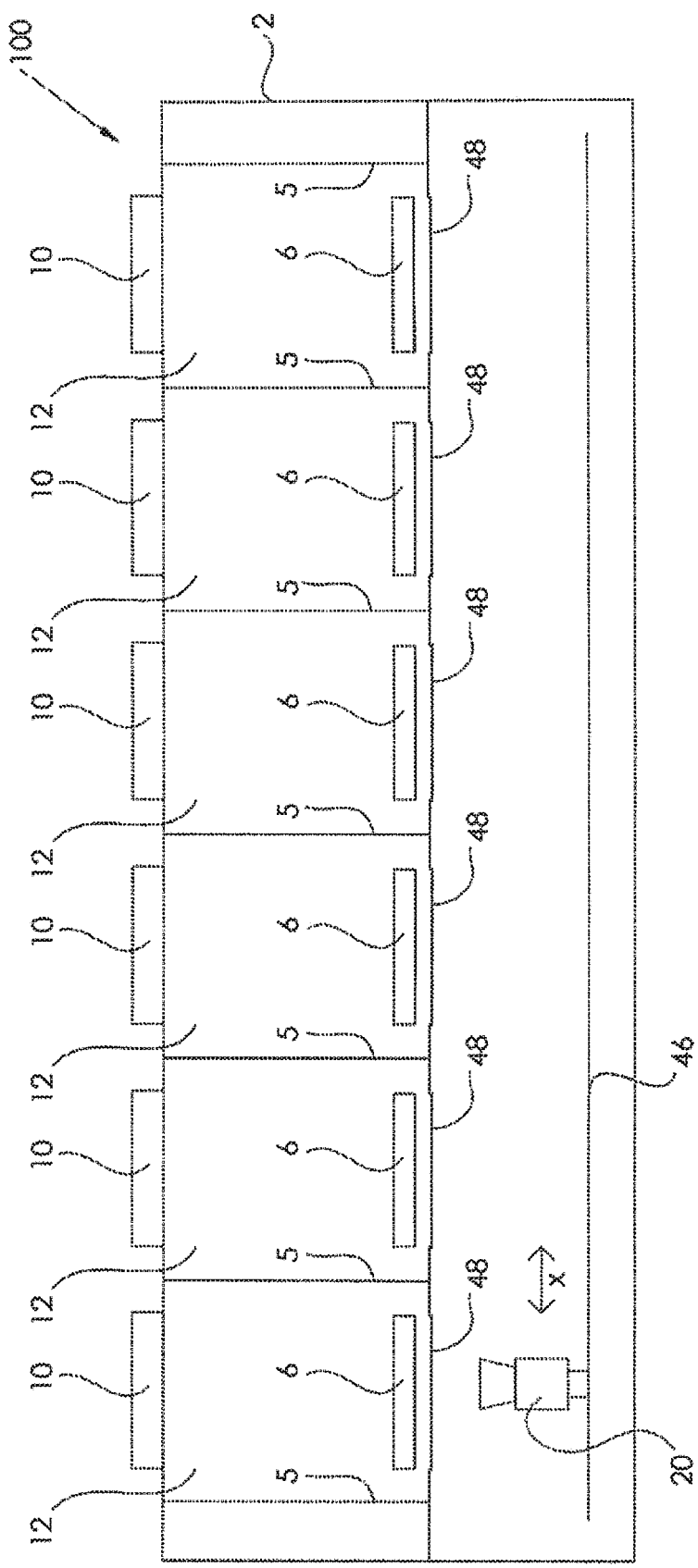
FIG. 2 shows schematically the principle of the device according to the first aspect of the present invention.

FIG. 2 shows schematically the principle of a device according to the first aspect of the present invention and shown in FIG. 1. FIG. 2 illustrates that the housing 2 of the device 100 comprises six separate culture dish compartments 4, each culture dish compartment being separated from the adjacent culture dish compartment 4 by a compartment wall 5. In FIG. 2 are shown that a culture dish 6 is accommodated in each culture dish compartments 4. The culture dish 6 rests on a shelf which in FIG. 2 simple is the bottom of the culture dish compartment. Part of the bottom 48 of the culture dish compartments are transparent, thus allowing the camera 20 to capture images of a biological material accommodated in one or more wells (not shown in FIG. 2) of the culture dishes from an area below the culture dish compartments 4.

The camera 20 is attached to camera moving means 46 which allows the camera 20 to move along the longitudinal direction X with the view to capture images of culture wells of one or more culture dishes arranged in one or more of the culture dish compartments 4.

It is seen in FIG. 2 that each culture dish compartment 12 is having its own dedicated lid 10 which allows for inspecting a culture dish accommodated in a specific compartment without imposing any adverse effects, such as altering the composition of atmosphere or altering the temperature of the atmosphere of any of the other culture dish compartments 4. Moreover, in this way no risk of contamination of the content of the culture dishes 6 in any other compartment 4 than the specific one subject to inspection will be present.

In most cases it will be appropriate to provide the device 100 with means for providing a desired gas atmosphere in each culture dish compartments 4. It will furthermore in most cases be appropriate to provide the device 100 with heating means and temperature sensors for regulating the temperature in each culture dish compartments 4. Preferably the device 100 will also be provided with control means for controlling such parameters.

Figure 3:
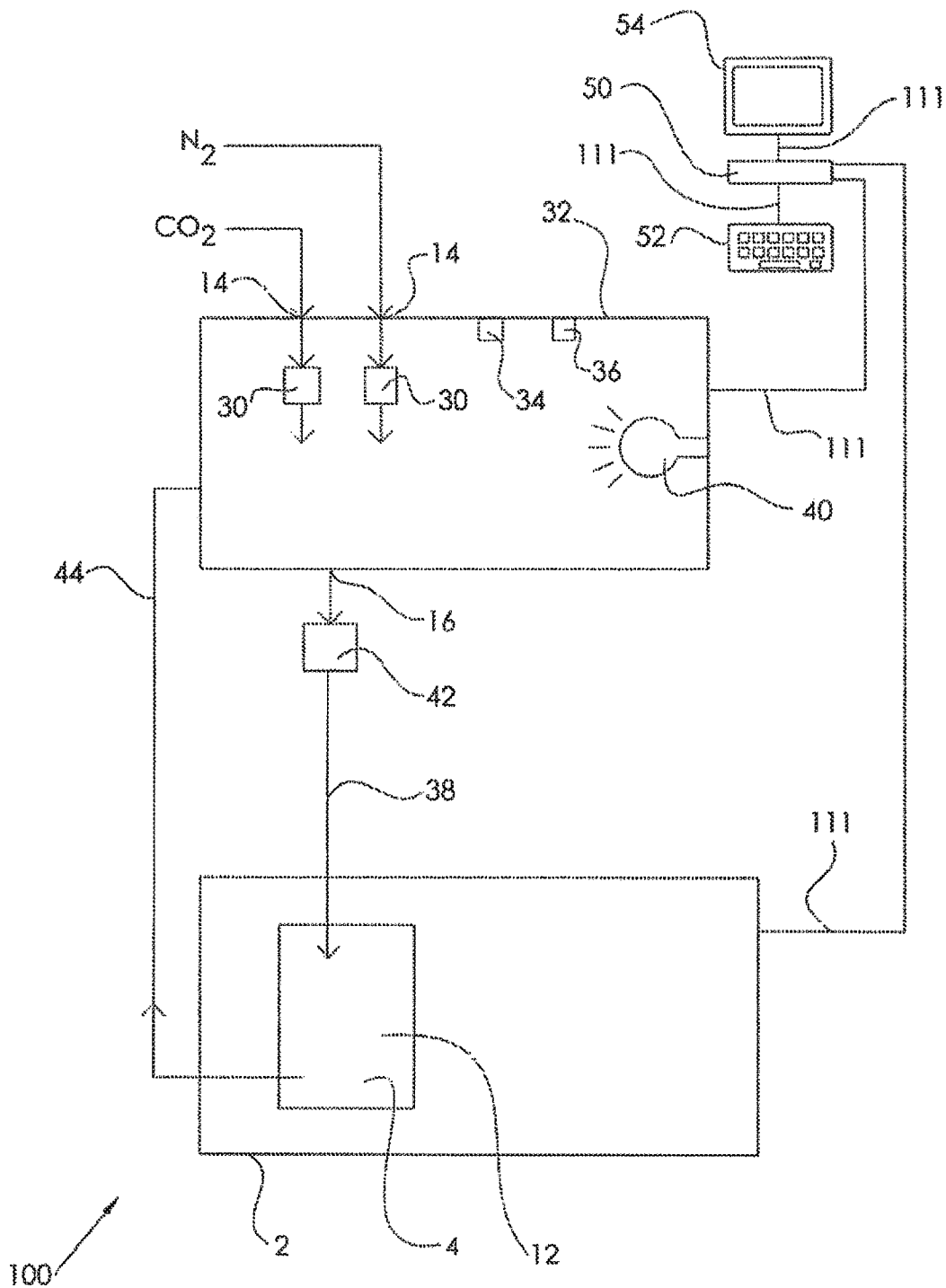
FIG. 3 schematically illustrates details of a control system of a device according to the first aspect of the present invention.

FIG. 3 illustrates schematically details of such a control system for the device 100 according to the first aspect of the present invention. FIG. 3 shows the device 100 comprising the housing 2. The housing comprises two or more separate culture dish compartments 4 (only one culture dish compartment 4 is shown in FIG. 3 for the sake of simplicity). The culture dish compartment 4 is provided with gas. The gas is flowing from a gas mixing box 32 in a conduit 38 through a filter means for gas 42 and into the interior 12 of the culture dish compartment 4.

In FIG. 3 various parts of the control system and the gas mixing box are indicated to be located outside the housing 2 of the device. This design may be possible. However, it may also be desirable to arrange such part inside the housing of the device.

The gas mixing box 32 comprises inlets 14 for gas. The gases to be supplied may preferably be $CO_2$ and $N_2$ as shown in FIG. 3. The magnitude of the flow of the gasses supplied to the gas mixing box may be regulated by the valves 30. Means 40 for emitting electromagnetic radiation in the UV wavelength range may be provided for gas sanitizing purposes.

The device may be provided with a control unit for controlling various parameters of the operation of the device. Such a control unit 50 is shown in FIG. 3. The control unit is coupled to input means 52, such as an alphanumerical keyboard or a pointing device allowing a user to input data relating to a desired mode of operation. Furthermore, the control unit may be coupled to display means 54 allowing a user to monitor various settings of the operation of the device. The items 111 designates means for mediation of information, such as electrical cables or wireless communication lines.

In FIG. 3 are also shown a $CO_2$ sensor 34 and an $O_2$ sensor 36. The sensors 32,34 may be coupled to the control unit 50 which in turn may be coupled to the valves 30 for regulating inlet of gas. In this way it will be possible to maintain a fairly constant atmosphere of a desired gas mixture in each separate culture dish compartment 4.

Each culture dish compartment 4 may be connected to its own dedicated gas mixing box 32; or alternatively, two or more culture dish compartments 4 may share the same gas mixing box 32.

Normally it will not be desired to provide oxygen content in the interior 12 of the culture dish compartments 4 above the normal oxygen level in atmospheric air. For this reason the oxygen level may be regulated by supplying varying amounts of $CO_2$ and $N_2$. The $CO_2$ level may in turn be regulated by "dilution" with $N_2$.

From the interior 12 of the culture dish compartment 4 is provided a conduit 44 for recirculating gas from the interior 12 of the compartment 4 back to the gas mixing box 32.

In the second aspect the present invention relates to a system 300 comprising a device 100 according to the first aspect according to the present invention combined with an image processing unit 200.

The image processing unit 200 comprises a data processor 110, an input device 112, such as an alphanumerical keyboard, allowing a user to input operation instructions; and a display 114 adapted to present information to a user.

Figure 4:
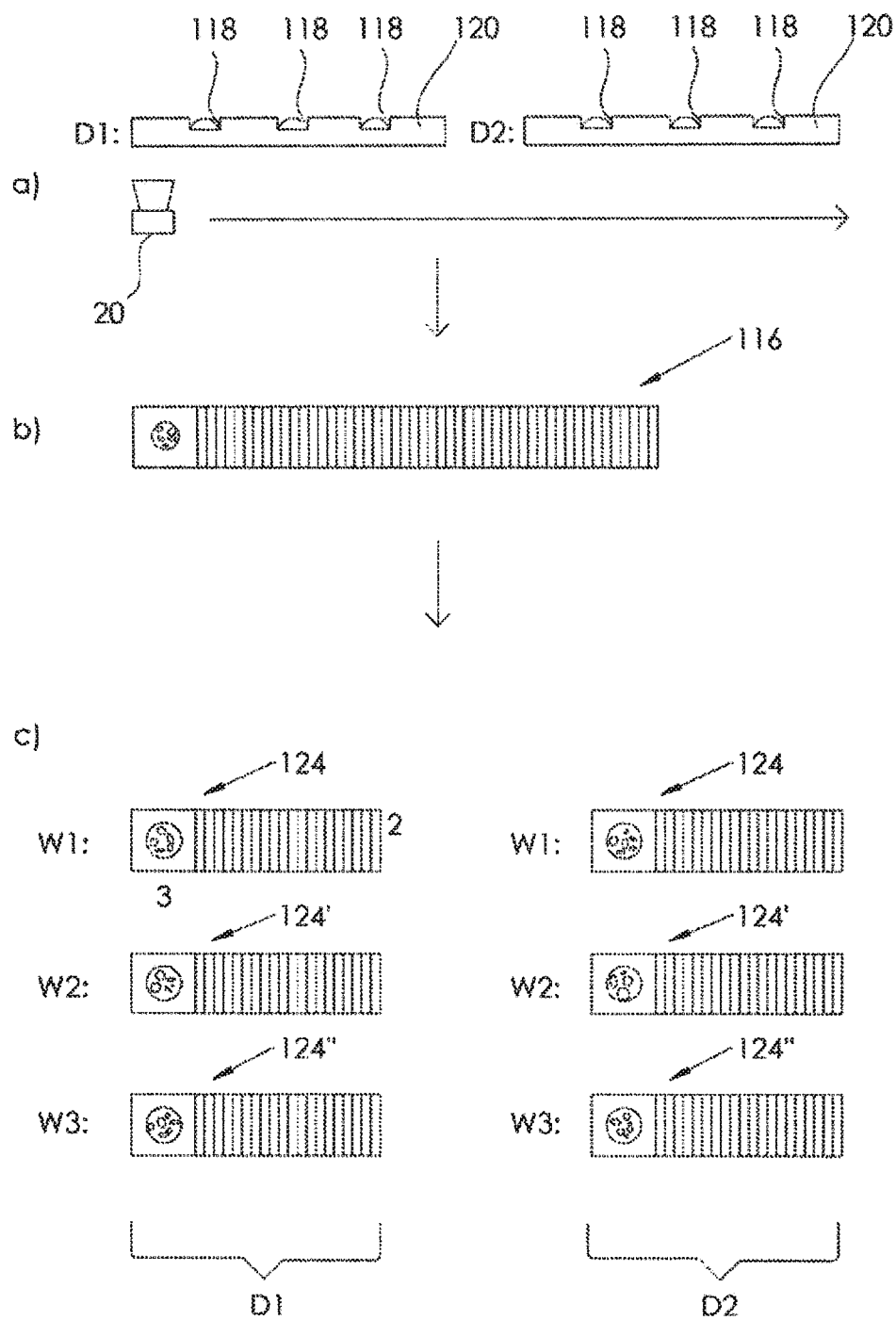
FIGS. 4, 5 and 6 illustrate schematically part of the principle of the image processing unit employed in a second aspect of the present invention.

In FIG. 4 is schematically illustrated part of the mode of operation of such an image processing unit 200.

FIG. 4a illustrates the operation of capturing images by a camera 20. In this specific example, the images relate to images of biological materials cultured in different culture wells 118 of two culture dishes D1 and D2. The camera 20 moves along a line defined by two or more of the culture wells 118 of the two culture dishes D1 and D2.

This will result in a range of chronologically captured images 116 as illustrated in FIG. 4b. The chronologically captured images 116 will not yet be sorted in respect of the individual wells 118 of the two dishes D1 and D2. The captured images 116 are only chronologically sorted.

The image processing unit 200 comprises means for sorting the images 116 according to a system in which the range of captured images 116 will be divided into six sets of time lapse series, wherein three sets 124, 124' and 124" respectively each relate to each well W1,W2 and W3 of the first culture dish D1 as illustrated in FIG. 4c. Another three sets 124, 124' and 124" respectively will each relate to each well W1,W2 and W3 of the first culture dish D1 as illustrated in FIG. 4c.

This may be easily accomplished on the basis of knowledge of the specific order of capturing images in respect of the various culture wells of the various culture dishes.

Accordingly, the image processing unit 200 comprises means for sorting the chronological, unsorted images 116 into time lapse series of images 124, 124' and 124", wherein each time lapse series relates to one culture well of the culture dishes in the device 100.

As the system according to the second aspect of the present invention and hence also the image capturing unit according to the third aspect of the present invention is especially intended for subjective assessment of the health and viability of a biological material subject to investigation, meaning that human decisions are to a large extent involved in selecting the biological material which seem to be most valuable, rather than relying on automated means for selecting this specific biological material, it will be desirably to provide the system and/or the image processing unit with means for presentation of information relating to the captured images.

Figure 5:
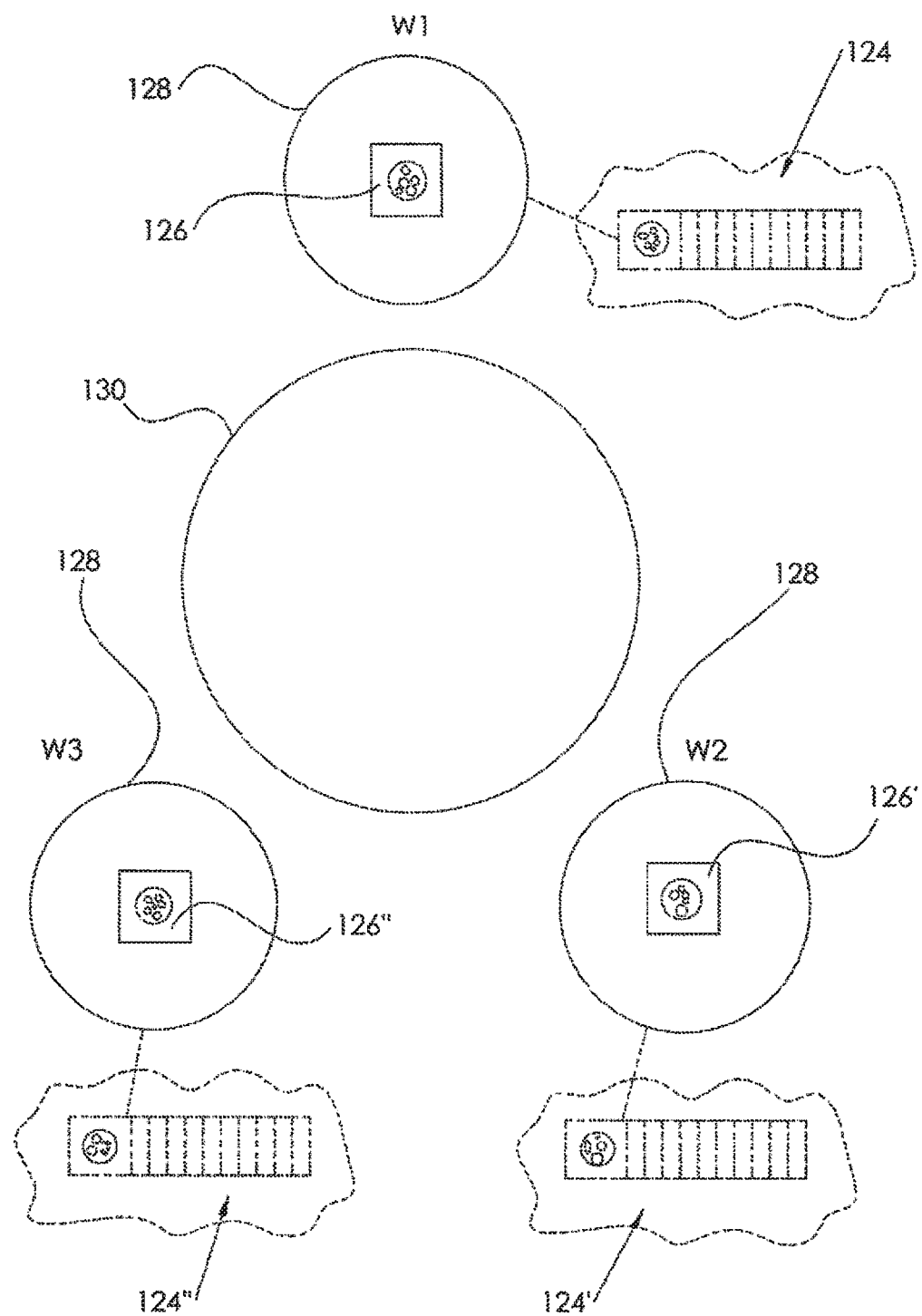
Figure 6:
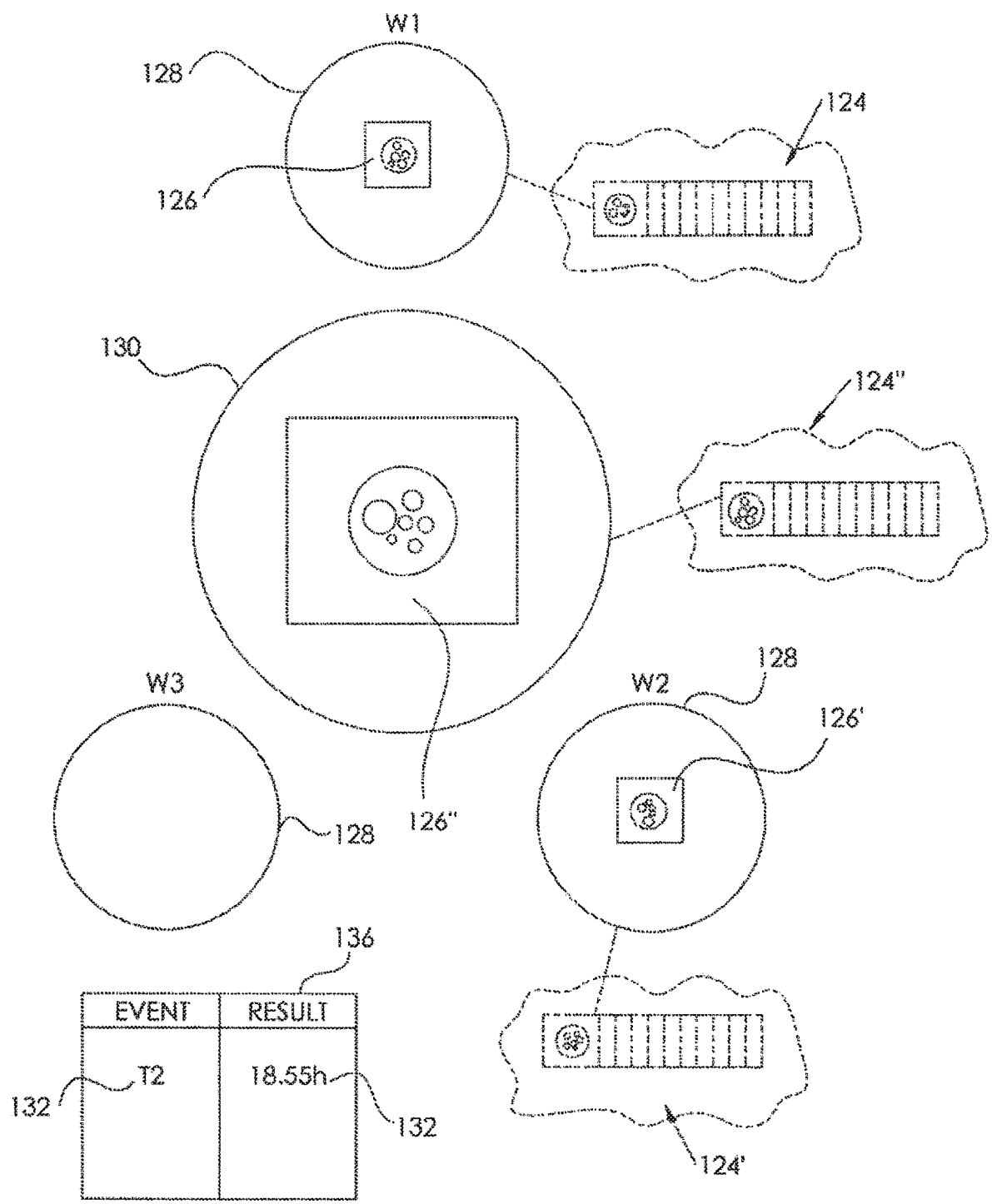

Such information presentation features are schematically illustrated in FIGS. 5 and 6.

In the case the time lapse series of images relate to time lapse images of an in vitro fertilized human egg it is customary to dedicate one culture dish to one single woman's eggs. Once the culture dish (D1 or D2) has been selected, the time lapse images (124,124',124") which are subject to further scrutiny, the image processing unit may be adapted to present the time lapse images 124,124,124" in a manner as shown in FIG. 5.

FIG. 5 illustrates a preferred way of presenting to a user information relating the captured time lapse images 124, 124',124" relating to images captured of a culture dish D1 having three culture wells 118 or W1,W2 and W3.

In FIG. 5 are seen four circles or windows. Three relatively small circles or windows 128 and one relatively large circle or window 130 are presented to the user on the display 114. In each relatively small window is shown one specific image 126, 126', 126" belonging to its respective series of time lapse images 124,124',124". Each image 126,126', 126" shows a single image of a human embryo conceived in an in vitro fertilization operation.

The image processing unit 200 is adapted to allow a user to select one of the time lapse series 124, 124', 124" being presented in its own dedicated relatively small window 128. This may be done by the input device 112, which may be an alphanumerical keyboard, a pointing device, such as a computer mouse, or a pressure sensitive monitor screen. The selected time lapse series 124, 124', 124" belongs to the images captured in respect of a specific single culture well of the culture dish D1.

By selecting a specific time lapse series, the image processing unit 200 is adapted to allow a user to take a closer look on that time lapse series which has specifically been selected.

This is illustrated in FIG. 6, which shows that the time lapse series 124" has been selected by a user for further scrutiny.

The image processing unit 200 is adapted to let a single image 126" of the selected time lapse series 124" appear as a magnified image in the relatively large window 130. Once appearing in the relatively large window 130, the image processing unit 200 is adapted to allow a user to scroll forward and backwards in the time lapse series 124" appearing in the relatively large window 130. When appearing in the relatively large window 130, the image 126,126', 126" associated with the time lapse series of images 124,124', 124" preferably disappears in its original small window 128.

Furthermore, the image processing unit 200 is adapted to allow a user to annotate individual images appearing in the relative large window 130.

This may be advantageous because important events in the development of the embryo under scrutiny may be noted and linked to the image in which that event happened.

The image processing unit 200 is adapted to link and store such annotations to one or more individual images of a time lapse series of images 124,124',124".

Furthermore, the image processing unit 200 is adapted to allow a user to edit and delete any annotation, whereafter the image processing unit 200 will save the amendments made.

In FIG. 6 is shown an annotation window 136 allowing a user to annotate the specific image being presented in the relatively large window 130.

In FIG. 6, a user has annotated the event of the cell division T2 at time 18.55 hours to the image 126" appearing in the relatively large window 130.

In case a user wishes to scrutinize a time lapse series of images associated with another culture well of the same culture dish, the image processing unit 200 is adapted to allow that user to simply select by the input device 112 the specific small window 128 relating to that time lapse series 124,124',124".

Subsequently, by means of the image processing unit 200, a specific image 126,126',126" belonging to that selected time lapse series 124, 124', 124" will appear in the relatively large window 130.

The dashes "clouds" merely is included in FIGS. 5 and 6 in order to illustrate that each image 126,126',126" belongs to its associated time lapse series 124,124',124". The content of "clouds" symbolically illustrating the time lapse series 124'124',124" may or may not be displayed to the user.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

LIST OF REFERENCE NUMERALS

2 Housing
4 Culture dish compartments
5 Compartment wall
6 Culture dish
8 Biological material
10 Lid of culture dish compartment
12 Interior of culture dish compartment
14 Inlet for gas
16 Outlet for gas
18 Heating means
20 Camera
22 Shelf of culture dish compartment
24 Temperature sensor
26 pH sensor
28 Connector for supplying gas
30 Valve for regulating inlet of gas
32 Gas mixing box
34 $CO_2$ sensor
36 $O_2$ sensor
38 Gas conduit
40 Means for providing UV radiation
42 Filter means for gas
44 Conduit for gas
46 Camera moving means
48 Bottom of culture dish compartment
50 Control unit
52 Input means
54 Display means
100 Device
111 Means for mediating information
110 Data processor
112 Input device
114 Display
116 Chronologically captured images of one image recording session
118 Culture well of culture dish
120 Culture dish
122 Group of images representing images belonging to same culture well
122' Group of images representing images belonging to same culture well
122" Group of images representing images belonging to same culture well
124 Time lapse series of images representing images belonging to same culture well
124' Time lapse series of images representing images belonging to same culture well
124" Time lapse series of images representing images belonging to same culture well
126 Individual image of time lapse series of images
126' Individual image of time lapse series of images
126" Individual image of time lapse series of images
128 Relatively small window on display
130 Relatively large window on display
132 Annotation
134 Marking of window
136 Annotation window
138 Ideal time lapse series of images
200 Image processing unit
300 System
400 Kit of parts
D1 First culture dish
D2 Second culture dish

The invention claimed is:

1. A device for incubating and monitoring the development of a biological material, said device in the orientation intended for use comprising:
    a housing having an extension in a longitudinal direction (X) and an extension in a transversal direction (Y), said housing comprises:
    two or more culture dish compartments, each adapted to accommodate a culture dish comprising a biological material to be monitored, each said culture dish compartment of said two or more culture dish compartments being separated from each of said other culture dish compartments of said two or more culture dish compartments, said two or more culture dish compartments being arranged along the longitudinal direction;
    each said culture dish compartment of said two or more culture dish compartments comprising a respective lid adapted to be able to be shifted between an open configuration in which access to the interior of said culture dish compartment is provided, and a closed configuration sealing off the interior of said culture dish compartment from its surroundings;
    wherein each said culture dish compartment of said culture dish compartments comprises an inlet for supplying a gas mixture to and an outlet for removing gas from said culture dish compartment;
    a gas mixing box for providing thorough mixing of two or more gases to form the gas mixture that is supplied to said culture dish compartment in order to provide a controlled gaseous atmosphere in said culture dish compartment for incubating the biological material in the culture medium having the pH value;
    wherein each said culture dish compartment of said culture dish compartments comprising heating means for heating the interior of said culture dish compartment;
    wherein said housing comprises one or more cameras for capturing images of a biological material in a culture dish; wherein said camera being configured for being moved along an area of a location of the two or more culture dish compartments and below the area of the location of the two or more culture dish compartments in a direction parallel to the longitudinal direction (X), and wherein in respect of one or more of said culture dish compartments at least part of the bottom of said culture dish compartments being transparent, thus allowing the camera to capture pictures of part of the culture dish from a position of said camera below said two or more culture dish compartments.

2. A device according to claim 1, wherein the number of culture dish compartments is between 3 and 20.

3. A device according to claim 1, wherein at least one said culture dish compartment comprises a shelf adapted to accommodate a culture dish, said shelf being provided with the heating means configured to heat said shelf.

4. A device according to claim 1, wherein the lid of at least one said culture dish compartment is provided with the heating means.

5. A device according to claim 1, wherein a temperature sensor is provided in at least one said culture dish compartment.

6. A device according to claim 1, wherein a pH sensor is provided in at least one said culture dish compartment.

7. A device according to claim 1, further comprising one or more connectors for supplying one or more types of different gases from an external source.

8. A device according to claim 7, wherein at least one of said one or more connectors is coupled to a valve located downstream of said connector for regulating the flow of gas into the apparatus.

9. A device according to claim 8, wherein a mixing box is located downstream in respect of said valve.

10. A device according to claim 9, wherein said mixing box comprises a CO2 sensor; and a O2 sensor, and furthermore comprises one or more conduits for conducting the gas mixture from said gas mixing box to one or more of said culture dish compartments.

11. A device according to claim 10, wherein two or more culture dish compartments share the same gas mixing box; or wherein each culture dish compartment is assigned its own individual gas mixing box.

12. A device according to claim 1, wherein said apparatus comprises a UV radiation light for subjecting said two or more gases to UV radiation, said UV radiation light optionally comprises a filter for filtering off UV radiation which could lead to the production of ozone.

13. A device according to claim 1, furthermore comprising a filter for filtering the two or more gases.

14. A device according to claim 1, further comprising one or more conduits for leading at least one gas from at least one said culture dish compartment to the gas mixing box.

15. A device according to claim 1, wherein at least one said culture dish compartment comprises one camera, said camera being configured to move along the area of the location of the two or more culture dish compartments within said two or more culture dish compartments; said camera being adapted to move in at least one direction.

16. A device according to claim 1, further comprising a control unit for measuring and/or controlling one or more parameters of the operation of said device.

17. A device according to claim 16, wherein said one or more parameters are selected from the group comprising: temperature in the interior of one or more of said culture dish compartments; O2 concentration in the in the interior of one or more of said culture dish compartments, CO2 concentration in the in the interior of one or more of said culture dish compartments, pH in a culture medium present in a culture dish, magnitude of gas flow, magnitude of gas pressure, number of lid openings and duration of time thereof in respect of each specific lid, parameters of said camera.

18. A device according to claim 16, wherein said control unit is coupled to an input device for allowing a user to define parameters of operation; and/or wherein said control unit is coupled to a display for providing information relating to the operation of the device to a user.

19. A system comprising a device according to claim 1 combined with an image processing unit;
    wherein said image processing unit comprises a data processor; an input device, such as an alphanumeric keyboard, allowing a user to input operation instructions; and a display adapted to present information to a user;
    wherein said image processing unit being configured to upload and store a number of images, said images being captured in a chronological order by a camera at different points in time, said images depicting different culture wells of a number of culture dishes;
    wherein said image processing unit is adapted to sort the images into a number of groups each group representing images associated with the same culture well;
    wherein said image processing unit in respect of each group of images is adapted to sort said images in a chronological time lapse series of images originating from the same culture well;

wherein said image processing unit is adapted to receive instructions from a user to present on said display, in respect of each culture well of a specific culture dish, an image belonging to a time lapse series of images associated with each of the culture wells of said specific culture dish, said specific culture dish being selected by a user;

wherein said image processing unit is adapted to present on said display, in respect of each culture well of said specific culture dish, an individual image belonging to a time lapse series of images associated with each of the culture wells of said specific culture dish selected by a user;

wherein said individual image being presented on said display in a relatively small "window";

wherein said image processing unit is adapted to allow a user to select amongst those relatively small "windows" a specifically selected individual image belonging to one time lapse series of images associated with a specific culture well of said selected culture dish;

wherein said image processing unit is adapted to present said specifically selected individual image belonging to one time lapse series of images associated with a specific culture well of said selected culture dish, wherein said specifically selected individual image being presented in a relatively large "window" on said display;

wherein said image processing unit is adapted to present said relatively large "window" on said display concurrently with presenting each of the relatively small "windows", each representing an image belonging to one time lapse series of images associated with the remaining culture wells of said selected culture dish;

wherein said image processing unit is adapted to receive instructions from a user relating to "playing" said time lapse series of images associated with said individual image being presented in said relatively large "window"; and wherein said image processing unit is adapted to, subsequently to "play" said time lapse series of images associated with said individual image being presented in said relatively large "window".

20. A system according to claim 19, wherein said image processing unit is adapted to receive instructions by a user to "play" said time lapse series of images associated with said individual image being presented in said relatively large "window" at a display rate selected by a user, said display rate being from 0.1 or more to 30 frames or less per second (fps), either in a chronological forward or a chronological backward direction.

21. A system according to claim 19, wherein said image processing unit is adapted to receive instructions by a user relating to present in said relatively large "window" an image belonging to another time lapse series of images than the one actually being represented in said relative large "window", and wherein said image processing unit is adapted to subsequently display an individual image belonging to said other time lapse series of images in said relatively large "window".

22. A system according to claim 19, wherein said image processing unit is adapted to received instructions by a user relating to one or more annotations of said specific image being displayed in said relatively "large window", wherein said image processing unit is adapted to subsequently link and store such one or more annotations to said specific image.

23. A system according to claim 22, wherein said image processing unit is adapted to present on said display, any annotations associated with said specific image being presented in said relatively large "window".

24. A system according to claim 22, wherein said image processing unit is adapted to allow a user to edit, store and delete one or more annotations of said specific image being displayed in said relatively "large window", wherein said image processing unit is adapted to subsequently link and store/delete such edition/deletion of one or more annotations to said specific image.

25. A system according to claim 22, wherein said image processing unit, in respect of anyone of said relatively small "windows", is adapted to present a marking of said relatively small "window" in the event that any annotations have been linked to one or more images in the time lapse series of images associated with the image presented in said relatively small "window", thus allowing a user to be informed that the time lapse series of images associated with said relatively small "window" has already been annotated.

26. A system according to claim 22, wherein said image processing unit is adapted to display one or more separate "windows" for presenting annotations associated with the specific image being presented in the relatively large "window".

27. A system according to claim 22, wherein said image processing unit is adapted to display the relatively small "windows" and the relatively large "window" in such a way that the relatively small "windows" surrounds the relatively large "window".

28. A system according to claim 22, wherein said image processing unit is adapted to allow a user to scroll the list of annotations and to select one annotation, wherein said image processing unit is adapted to subsequently display in the relatively large "window", the specific image linked to said selected annotation.

29. A system according to claim 22, wherein said image processing unit is adapted to have stored in a memory an "ideal time lapse series" corresponding to an ideal development over time, and wherein said image processing unit is adapted to present on said display, upon being instructed thereto, such an "ideal time lapse series", optionally as a superimposition of a time lapse series of images corresponding to said specifically selected culture well one the one hand, and said "ideal time lapse series" on the other hand.

30. A system according to claim 22, wherein said "ideal time lapse series" is an authentic time lapse series or is an animated time lapse series or a combination thereof.

31. An image processing unit comprising:
a data processor: an input device, such as an alphanumeric keyboard, allowing a user to input operation instructions: and a display adapted to present information to a user;

wherein said image processing unit being configured to upload and store a number of images, said images being captured in a chronological order by a camera at different points in time, said images depicting different culture wells of a number of culture dishes;

wherein said image processing unit is adapted to sort the images into a number of groups each group representing images associated with the same culture well;

wherein said image processing unit in respect of each group of images is adapted to sort said images in a chronological time lapse series of images originating from the same culture well;

wherein said image processing unit is adapted to receive instructions from a user to present on said display, in respect of each culture well of a specific culture dish, an image belonging to a time lapse series of images associated with each of the culture wells of said specific culture dish, said specific culture dish being selected by a user;

wherein said image processing unit is adapted to present on said display, in respect of each culture well of said specific culture dish, an individual image belonging to a time lapse series of images associated with each of the culture wells of said specific culture dish selected by a user:

wherein said individual image being presented on said display in a relatively small "window";

wherein said image processing unit is adapted to allow a user to select amongst those relatively small "windows" a specifically selected individual image belonging to one time lapse series of images associated with a specific culture well of said selected culture dish;

wherein said image processing unit is adapted to present said specifically selected individual image belonging to one time lapse series of images associated with a specific culture well of said selected culture dish, wherein said specifically selected individual image being presented in a relatively large "window" on said display;

wherein said image processing unit is adapted to present said relatively large "window" on said display concurrently with presenting each of the relatively small "windows", each representing an image belonging to one time lapse series of images associated with the remaining culture wells of said selected culture dish:

wherein said image processing unit is adapted to receive instructions from a user relating to "playing" said time lapse series of images associated with said individual image being presented in said relatively large "window"; and wherein said image processing unit is adapted to, subsequently to "play" said time lapse series of images associated with said individual image being presented in said relatively large "window".

32. A kit of parts comprising a device according to claim 1, combined with a number of culture dish configured to contain a biological material to be monitored.

33. A kit of parts according to claim 32, said culture dish having culture well depressions arranged on an essentially straight line.

34. A kit of parts according to claim 32, wherein said culture dish comprises from 4 or more to 26 or less culture well depressions.

35. A device according to claim 1, wherein the two or more gases comprise $CO_2$ and $N_2$ gases.

36. A device according to claim 1, wherein said gas mixing box is in fluid communication with a first conduit for delivering the gas mixture of two or more gases to said culture dish compartment and a second conduit for recirculating the gas mixture of two or more gases from the culture dish compartment to the gas mixing box.

* * * * *